(12) United States Patent
Ierulli

(10) Patent No.: US 8,444,670 B2
(45) Date of Patent: *May 21, 2013

(54) NASAL DILATOR WITH MEANS TO DIRECT RESILIENT PROPERTIES

(75) Inventor: Joseph V. Ierulli, Portland, OR (US)

(73) Assignee: Corbett Lair, Inc., Milwaukie, OR (US)

( * ) Notice: Subject to any disclaimer, the term of this patent is extended or adjusted under 35 U.S.C. 154(b) by 34 days.

This patent is subject to a terminal disclaimer.

(21) Appl. No.: 13/206,462

(22) Filed: Aug. 9, 2011

(65) Prior Publication Data

US 2011/0295312 A1    Dec. 1, 2011

Related U.S. Application Data

(63) Continuation of application No. 12/106,289, filed on Apr. 19, 2008, now Pat. No. 8,062,329.

(60) Provisional application No. 60/913,271, filed on Apr. 21, 2007.

(51) Int. Cl.
*A61F 5/08* (2006.01)
(52) U.S. Cl.
USPC .................................. 606/204.45; 128/200.24
(58) Field of Classification Search
USPC ............. 606/204.45, 199; 128/200.24; 602/5, 602/6; D24/135, 189
See application file for complete search history.

(56) References Cited

U.S. PATENT DOCUMENTS

| | | |
|---|---|---|
| 5,476,091 A | 12/1995 | Johnson |
| 5,479,944 A | 1/1996 | Petruson |
| 5,533,499 A | 7/1996 | Johnson |
| 5,533,503 A | 7/1996 | Doubek et al. |
| 5,546,929 A | 8/1996 | Muchin |
| 5,549,103 A | 8/1996 | Johnson |
| RE35,408 E | 12/1996 | Petruson |
| 5,611,333 A | 3/1997 | Johnson |
| 5,653,224 A | 8/1997 | Johnson |
| 5,706,800 A | 1/1998 | Cronk et al. |
| 5,718,224 A | 2/1998 | Muchin |
| 5,769,089 A | 6/1998 | Hand et al. |

(Continued)

FOREIGN PATENT DOCUMENTS

ES    289561    10/1985

*Primary Examiner* — Katherine Dowe
(74) *Attorney, Agent, or Firm* — Mersenne Law LLC

(57) ABSTRACT

A nasal dilator comprises a laminate of vertical layers each consisting of one or more members or components. The laminated layers form a unitary, or single body, truss featuring horizontal regions adapted to engage outer wall tissues of first and second nasal passages and to traverse the bridge of a nose therebetween. When in use the dilator acts to stabilize and/or expand the nasal outer wall tissues and prevent said tissues from drawing inward during breathing. The dilator includes means to direct its resilient properties comprising one or more interior or exterior material separations, or discontinuity of shape of material, formed in at least one region of the truss and extending through at least one layer of the dilator. Said material separation or discontinuity of shape may comprise an opening, relief cut, slit or notch, and which may be configured to separate or vertically protrude, in part, from the truss when the dilator is in use on the nose of a wearer. Said separation or vertical protrusion changes the angle of focused delaminating spring biasing forces generated by the resilient layer, transforming said forces, at least in part, from primarily peel forces into primarily shear forces, and further redistributing or imparting said transformed forces to tissue engaging surface areas extending outward and beyond said material separation.

8 Claims, 8 Drawing Sheets

U.S. PATENT DOCUMENTS

| | | | |
|---|---|---|---|
| 5,890,486 | A | 4/1999 | Mitra et al. |
| 5,931,854 | A | 8/1999 | Dillon |
| 5,957,126 | A | 9/1999 | Neeser |
| 6,006,746 | A | 12/1999 | Karell |
| 6,029,658 | A | 2/2000 | De Voss |
| 6,058,931 | A | 5/2000 | Muchin |
| 6,065,470 | A | 5/2000 | Van Cromvoirt et al. |
| 6,098,616 | A | 8/2000 | Lundy et al. |
| 6,196,228 | B1 | 3/2001 | Kreitzer et al. |
| 6,244,265 | B1 | 6/2001 | Cronk et al. |
| 6,276,360 | B1 | 8/2001 | Cronk et al. |
| 6,318,362 | B1 | 11/2001 | Johnson |
| 6,352,548 | B1 * | 3/2002 | Blach et al. .................. 606/199 |
| 6,357,436 | B1 | 3/2002 | Kreitzer et al. |
| 6,375,667 | B1 | 4/2002 | Ruch |
| 6,453,901 | B1 | 9/2002 | Ierulli |
| 6,550,474 | B1 | 4/2003 | Anderson et al. |
| 6,694,970 | B2 | 2/2004 | Spinelli et al. |
| 6,769,428 | B2 | 8/2004 | Cronk et al. |
| 6,769,429 | B1 | 8/2004 | Benetti |
| 7,067,710 | B1 | 6/2006 | Beaudry |
| 7,114,495 | B2 | 10/2006 | Lockwood, Jr. |
| D639,762 | S | 6/2011 | Brogden et al. |
| 2005/0247317 | A1 * | 11/2005 | Lockwood, Jr. ......... 128/206.11 |
| 2007/0255309 | A1 | 11/2007 | Guyuron et al. |
| 2008/0058858 | A1 | 3/2008 | Smith |
| 2008/0097517 | A1 | 4/2008 | Holmes et al. |
| 2009/0020115 | A1 | 1/2009 | Lockwood, Jr. |
| 2009/0048626 | A1 | 2/2009 | Beaudry |
| 2009/0125052 | A1 | 5/2009 | Pinna et al. |
| 2011/0000483 | A1 | 1/2011 | Matthias et al. |

* cited by examiner

NASAL DILATOR WITH MEANS TO DIRECT RESILIENT PROPERTIES

RELATED APPLICATIONS

This application is a CONTINUATION of Nonprovisional patent application Ser. No. 12/106,289 filed 19 Apr. 2008, now U.S. Pat. No. 8,062,329, which claims priority benefit of Provisional Patent Application No. 60/913,271 filed 21 Apr. 2007.

FIELD OF THE INVENTION

The present invention relates to apparatus and methods of dilating external tissue. As disclosed and taught in the preferred embodiments, the tissue dilator devices are particularly suitable for use as external nasal dilators for supporting, stabilizing, and dilating nasal tissues adjacent and overlying nasal airway passages, including the nasal valve and/or the vestibule areas thereof.

BACKGROUND OF THE INVENTION

A portion of the human population has some malformation of the nasal passages which interferes with breathing, including deviated septa and swelling due to allergic reactions. A portion of the interior nasal passage wall may draw in during inhalation to substantially block the flow of air through the nasal passage. Blockage of the nasal passages as a result of malformation, symptoms of the common cold or seasonal allergies are particularly uncomfortable at night, and can lead to sleep disturbances, irregularities and general discomfort.

Spring-based devices for dilating outer wall tissues of the human nose adjacent the nasal passages have a history spanning over one hundred years. The spring-based concept uses resilient means which flex across the bridge of the nose together with means to engage the nasal passage outer walls from either the interior mucosa or exterior epidermis sides thereof and thus stabilize or urge outwardly the nasal outer wall tissue. Some examples of present external nasal dilators are disclosed in U.S. Pat. Nos. 6,453,901; D379,513; D429,332; D430,295; D432,652; D434,146; D437,64; and Japanese patent Reg. No. 1037944; the entire disclosures of which are incorporated herein by reference. The commercial success of at least one of these inventions, together with that of other modern external nasal dilators, collectively and commonly referred to as nasal strips, has led to the creation and establishment of a nasal dilator product category in the present consumer retail marketplace. Commercial success of prior art nasal dilator devices disclosed before 1990, in particular that of U.S. Pat. No. 1,292,083 (circa 1919), is presumed to be commensurate with the nature of consumer product retail environments at the time of those inventions.

Throughout the history of those medical devices which engage external bodily tissue (i.e., tissue dilators, nasal splints, ostomy devices, surgical drapes, etc.), a long-standing practice in the construction and use thereof has been to interpose a buffer material between the device and the user's skin to facilitate engagement of the device to the skin and to aid user comfort. Said material, such as a spunlaced polyester nonwoven fabric, typically has properties which permit limited, primarily plastic and somewhat elastic deformation within the thickness thereof. These properties can spread out peeling, separating or delaminating forces such as may be caused by gravity acting on the weight of the device; the device's own spring biasing force or rigidity (such as that of a tissue dilator or nasal splint); biasing force that may be present in bodily tissue engaged by the device; surface configuration differences between the device and the skin of the device wearer; displacement of the device relative to the skin or external tissue as a result of shear, tensile, cleavage and/or peel forces imparted thereat via wearer movement (e.g., facial gestures) and/or contact with an object (e.g., clothing, pillow, bedding, etc.); and so on, that may cause partial or premature detachment of the device from the wearer. By spreading out these delaminating forces, said interface material acts as a buffering agent to prevent the transfer of said forces to its adhesive substance, if any, and thereby to the skin. Preventing the transfer of focused delaminating forces substantially eliminates any itching sensation (caused by the separation of the adhesive substance or device from the skin) that a wearer may experience if these delaminating forces were otherwise imparted directly to the skin.

There has been a continuing need in the art to develop nasal dilators which address and improve upon the dynamics and design parameters associated with limited skin surface area adjacent the nasal passages, adhesive attachment, delaminating spring biasing forces, device comfort, and durational longevity.

Firstly, tissues associated with and adjacent the nasal passages have limited skin surface areas to which dilation may be applied. Said surfaces extend upward from the nostril opening to the cartilage just above the nasal valve, and extend outward from the bridge of the nose to each approximate line where the sides of the nose meet each cheek.

Secondly, nasal dilators are, of necessity, releasably secured to said skin surfaces by use of pressure sensitive adhesives. Skin surfaces transmit moisture vapor to the surrounding atmosphere. Said adhesives break down in the presence of skin oils, moisture and the transmission of moisture vapor, often within hours.

Thirdly, the functional element of present and historic spring-based nasal dilator devices designed to engage and stabilize and/or expand nasal outer wall tissue is a semi-rigid resilient member which extends beyond each side of the bridge of the nose adjacent the nostrils. External nasal dilator devices of the present modern era feature a flat, substantially rectangular or slightly arcuate resilient member made of plastic. When engaged to a nose, the resilient member exerts a spring biasing force which tends to substantially return or restore the device to an original, generally planar, state thus dilating the local tissue. Said spring biasing force creates primarily peel and some tensile forces generated at the end regions of the device where engaged to the nose of a wearer. Said forces work to delaminate the end regions of the dilator device from skin surfaces so engaged.

Constructing a device with less than 10 grams of spring biasing force in order to mitigate delaminating peel forces may not provide suitable stabilization to, or dilation of, nasal outer wall tissues. Over-engineering the dilator by using a more aggressive adhesive, a greater amount of adhesive, or greater adhesive surface area in order to withstand greater spring biasing force increases the likelihood of user discomfort during use and damage to the tissue upon removal of the device. Additionally, a dilating spring biasing force of 40 grams or more could, in and of itself, be uncomfortable for most users.

Presently known spring-based nasal dilator devices which are suitable or adaptable for mass commercialization in the present consumer retail market typically fall within a range of dimensions of 5.0 to 7.5 cm (2.0" to 3.0") in length and 1.2 to 2.5 cm (0.5" to 1.0") in width. Resilient members are typically from about 4.2 to 5.8 cm (1.7" to 2.3") long, approximately 0.048 to 0.12 cm (0.12" to 0.30") wide and typically 0.010"

thick. A resilient member thickness of more or less than 0.010" is not common in the art, but may be incorporated with proportionate adjustments to width and length. Examples include devices disclosed in U.S. Pat. Nos. D379,513; 5,533,503; 5,546,929; RE35408; 6,453,901; 7,114,495; and Spanish Utility Model 289-561 for Orthopaedic Adhesive. These devices provide sufficient dilation of nasal passage outer wall tissues and thus provide the claimed benefit to the vast majority of users. In addition, the '503 and '901 disclosures teach means for shifting, transforming and redistributing delaminating peel and tensile forces into primarily shear forces. Said shifting or transforming is desirable since the pressure sensitive adhesive disposed on nasal dilator devices for engaging skin surfaces adjacent the nasal passages withstand shear forces generally better, longer and more reliably than peel forces.

The '503 device features a complicated structure at the device lateral end edges whereby to shift, transform or redistribute said delaminating peel and tensile forces. Said structure includes first and second parallel, spaced apart, resilient spring bands with identical scalloped end edges forming upper and lower protrusions separated by a valley. The extent of said protrusions are defined by the respective ends of the resilient bands. Outboard and adjacent said upper and lower protrusions are respective upper and lower extensions separated from said protrusions by upper and lower back cuts. Said extensions extend past said protrusions. The '503 specification teaches that the constituent features of this end edge structure combine to effectively minimizes significant inadvertent peeling of the device end regions from the outer wall tissue of the nasal passages as a result of the discontinuity of shape of the materials at the intersection of said protrusions and said extensions, as defined by said back cuts, and redistributes and transforms peeling and tensile delaminating forces into primarily shear forces which are imparted to said upper and lower extensions extending beyond said back cuts.

The '901 disclosure teaches a simpler end region structure which includes relief cuts placed adjacent each terminal end of a single resilient spring band, extending around its terminal ends and slightly along the upper and lower longitudinal edges thereof, corresponding to the general outline of the terminal ends of the resilient band without contact thereto. When in use on the nose of a wearer, this structure shifts peel and tensile delaminating forces into primarily shear forces which are imparted to the material extending between said relief cuts and the lateral end edges of the device.

U.S. Pat. No. 5,611,333 discloses a dilator device which features various openings, slits, notches and cuts formed within the peripheral edges of a resilient member whereby to selectively reduce spring biasing forces locally so that the resilient member may be used as a stand alone dilator device without the use of additional materials for maintaining the dilator device engaged to the nose of a wearer.

The present invention builds upon the prior art by providing means to direct the resilient properties of a nasal dilator whereby to overcome the aforementioned dynamics and design parameters associated with external dilation of nasal outer wall tissues.

SUMMARY OF THE INVENTION

The present invention teaches, depicts, enables, illustrates, describes and claims new, useful and non-obvious apparatus and methods of providing dilation to external tissue. In particular, the present invention provides a wide variety of tissue dilators adapted to engage an exterior tissue region of a nose to dilate the nasal passages thereof, including the vestibule and/or nasal valve areas. It is the principal objective of the present invention to provide nasal dilator devices which improve and build upon the prior art and address unmet needs in the art.

In the specification and claims herein, the term vertical refers to a direction parallel to the thickness of the dilator or truss. The term horizontal refers to a direction parallel to the length, or longitudinal extent, or long axis of the dilator or truss. The term lateral refers to the width or opposing end edges of the dilator or truss, or a direction perpendicular to the length, longitudinal extent, or long axis of the dilator or truss. The term longitudinal centerline refers to a line parallel to the longitudinal extent of the dilator or truss, bisecting the width of the dilator or truss midway between its upper and lower long edges. The term lateral centerline refers to a line perpendicular to the length, longitudinal extent, or long axis of the dilator or truss, bisecting the long axis, or upper and lower long edges, midway along the length thereof.

The external nasal dilator of the present invention comprises a laminate of vertical layers. The laminated layers form a unitary, or single body, truss with each layer consisting of one or more members and/or components. The layers preferably include a base layer, resilient layer, and cover layer. Any single layer, or a combination of two or more layers may define the peripheral shape or edges of the dilator. The dilator is die cut from a continuous laminate of material layers, and dilator members or components may be die cut, in whole or part, from one or more continuous material layers before or during assembly of the continuous laminate. The truss features horizontal regions including first and second end regions adapted to engage outer wall tissues of first and second nasal passages, respectively, and an intermediate region adapted to traverse a portion of a nose located between the first and second nasal passages and joining the end regions. In use the dilator acts to stabilize and/or expand the nasal outer wall tissues and prevent said tissues from drawing inward during breathing.

Embodiments of the nasal dilator of the present invention include, without limitation, new and non-obvious means to direct the resilient properties thereof. Said means include one or more material separations, or discontinuity of shape of material, formed within the peripheral edges of the truss (an interior material separation), and may include one or more material separations or discontinuity of shape of material extending inward from a peripheral edge of the truss (an exterior material separation). Said material separations may be formed before, during or after the peripheral shape of the dilator is die cut from the aforementioned continuous laminate of materials. An interior material separation may also include forming, modifying or configuring at least a portion of the resilient layer before assembling the constituent layers of the dilator into the vertical laminate. Said formation, modification or configuration may include forming the peripheral shape of the resilient member, such as gradiently tapering its width, or may include forming component extensions such as spring fingers, or may include interior or exterior material separations, such as a cut, opening or notch, as described above with respect to the truss, but made to the resilient member alone.

An interior material separation may form a flap capable of separating or vertically protruding, in part, from the truss when the dilator is flexed across the nose of a wearer. Similarly, an exterior material separation may form a horizontal protrusion, also capable of separating, in part, from the truss when the dilator is flexed across the nose of a wearer. In either case, said separation or vertical protrusion changes the angle of focused spring biasing forces, at least in part, and thus shifts or transforms at least some of said forces from primarily peel and tensile forces to primarily shear forces. Said change in angle further redistributes or imparts said transformed forces to tissue engaging surface areas extending beyond the material separation. Thus, spring biasing forces may be distributed to the potentially larger surface area of the dilator end regions, as opposed to a greater delaminating tendency, such as that from peel forces, being imparted to a smaller surface area. Said potential larger surface area is as a result of the configuration of the end regions of the truss and/or the configuration of the respective layers of the dilator. The effect of material separations can lessen overall delaminating forces without reducing the spring biasing force of the dilator, in that shear forces are more easily withstood by the tissue engaging adhesives typically disposed on the tissue engaging surfaces of the dilator. Accordingly, a lesser amount of adhesive and/or less aggressive adhesive (and thus less costly) disposed on the tissue engaging surfaces of the dilator would, in addition, be more comfortable to the user and more easily removed from the tissue so engaged. An opposing pair of said material separation may be spaced apart along the longitudinal centerline of the truss.

An interior material separation extending vertically through the dilator, including the resilient layer, may also form a flap capable of separating or vertically protruding, in part, from the resilient layer. Said separation or vertical protrusion may also change, at least in part, the angle of spring biasing forces thereof, while allowing spring biasing forces to continue along a further extent of the resilient member or component. Said interior material separation may be confined within the peripheral edges of the resilient layer material or, alternatively, may sever the resilient member from one long edge thereof and extend across a portion of its width.

Means to direct resilient properties thus also include a dynamic relationship between the effects of interior and exterior material separations, including the degree of horizontal spacing between an opposing pair thereof, and any other modification to, or configuration of, the resilient layer, such as its peripheral shape or the inclusion of additional material separations made thereto.

The preferred embodiments of the present invention further include a truss with means for horizontally aligning the dilator to the nose of a wearer comprising a positioning aid located at the intermediate region forming a separation, projection or other index marker; means to spread the spring biasing force of resilient layer to a greater, primarily lateral, surface area of dilator, and means to prevent one or more material separations from separating in part from the truss. This latter means may also be used to extend or increase the tissue engaging surface area of the truss.

The skilled man in the art will appreciate the applicability of the continually developing art of medical device converting; specifically, continuous rotary laminating and die cutting, and flatbed and class A tool die cutting and punching.

The present invention is not limited to the illustrated or described embodiments as these are intended to assist the reader in understanding the subject matter of the invention. The preferred embodiments are examples of forms of the invention comprehended by the devices taught, enabled, described, illustrated and claimed herein. All structures and methods which embody similar functionality are intended to be covered hereby. In certain instances, the devices depicted, taught, enabled and disclosed herein represent families of new, useful and non-obvious tissue dilators having a variety of alternate embodiments. The skilled man will appreciate that features, devices, elements, members or components thereof, methods, processes or techniques may be applied, interchanged, eliminated in whole or part, or combined from one embodiment to another. Dilator members or components thereof, materials, layers or regions may be of differing size, area, thickness, length or shape than that illustrated or described while still remaining within the purview and scope of the present invention. The preferred embodiments include, without limitation, the following numbered, discrete forms of the invention, as more fully described below.

BRIEF DESCRIPTION OF THE SEVERAL VIEWS OF THE DRAWING

In the drawings which accompany this disclosure, like elements are referred to with common reference numerals. Drawings are not rendered to scale.

DETAILED DESCRIPTION OF THE INVENTION

Figure 1:
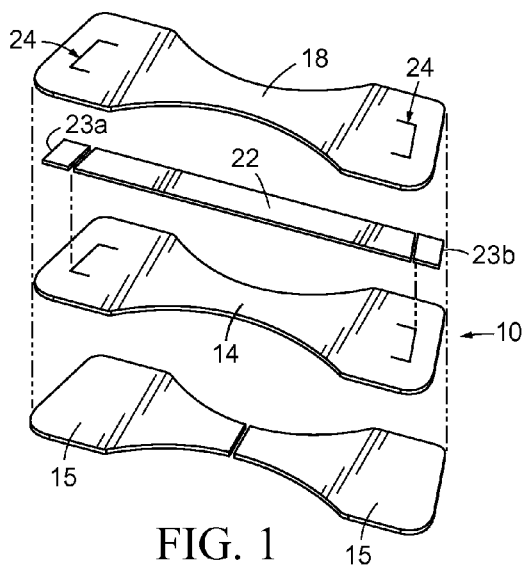
FIG. 1 is an exploded perspective view of a nasal dilator in accordance with the present invention.

An embodiment of a nasal dilator, 10, in accordance with the present invention is illustrated in FIG. 1. Dilator 10 comprises a vertical laminate of material layers including: a base layer composed of at least one base member, 14, including components thereof; a resilient layer comprised of at least one resilient member, 22, including components thereof; and a cover layer composed of at least one cover member, 18, including components thereof. A protective layer of release paper liner, 15, removably covers any exposed adhesive from any layer preliminary to use of dilator 10 on the nose of a wearer. The periphery of release liner 15 may correspond to the periphery of dilator 10 or a periphery exceeding one or more dilators 10. The components or layers of dilator 10 are preferably aligned along their longitudinal centerlines.

The preferred material for the base and cover layers is from a group of widely available flexible nonwoven synthetic fabrics that allow the skin on user nose 11 to exchange gases with the atmosphere and to maximize comfort of dilator 10 thereon. Alternatively, any suitable fabric or plastic film may be used. A continuous pressure sensitive adhesive substance, biocompatible with external human tissue, is disposed on at least one flat surface side of said material which is the adhesive side, opposite the non-adhesive side. The non-adhesive side is typically opposite the skin engaging side. A protective layer of continuous release paper liner covers said adhesive. Said materials are typically available in continuous rolls wound in a machine direction (MD) or warp, which is perpendicular to the cross direction (XD) or fill, of the fabric. The base and cover layers of dilator 10 may be fabricated parallel to either the warp or the fill of said fabrics. The preferred material for the resilient layer is a biaxially oriented polyester resin (PET). PET has suitable spring biasing properties both MD and XD, and is widely available under trade names such as Mylar® and Melinex® in a variety of standard thickness including 0.005", 0.007", and 0.010".

The width, length and peripheral outline or edges of dilator 10 may be defined by the base layer, cover layer, or a combination of any two or more layers or portions thereof. The base and cover layers of dilator 10 may have like or dissimilar dimensions or peripheral edges, in whole or in part, compared to each other. Their respective peripheral shapes may be uniform or non-uniform, and may also be of like or dissimilar size or scale. Portions of any layer may define a horizontal region of the dilator or a portion thereof. Furthermore, the base and cover layers of dilator 10 may be interchanged, or either the base layer or cover layer may be optionally eliminated in whole or in part. The base and resilient layers may have identical peripheral edges, and thus may be formed as a single unit. Portions of one or both flat surfaces of any layer, member or component thereof, may overlap portions of any flat surface of another layer. Preferably, however, the base layer acts as a buffer in engaging the user's skin, as described hereinbefore with respect to medical devices, and portions of one or more dilator layers may engage nasal outer wall tissues simultaneously. When engaged on the nose of a wearer, preferably no portion of a layer extends substantially over a skin surface area beyond those surface areas associated with the nasal passages as described hereinbefore.

Figure 2:
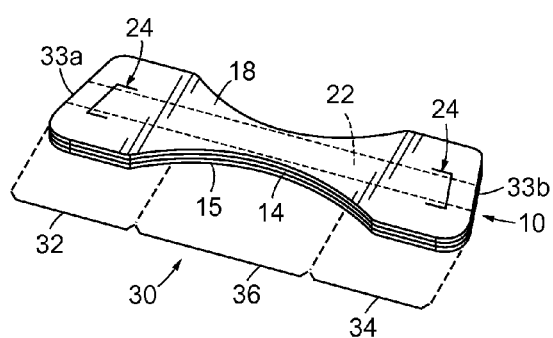
FIG. 2 is a perspective view of the nasal dilator of FIG. 1.

As illustrated in FIG. 2, the laminated layers of dilator 10 form a unitary, or single body, truss, 30, having horizontal regions as indicated by bracketed broken lines. Truss 30 includes a first end region, 32, a second end region, 34, and an intermediate region, 36, interconnecting first end region 32 to second end region 34. The layers, members or components of dilator 10 may overlap or extend from their originating region to an adjacent region. End regions 32 and 34 are adapted to engage outer wall tissues of first and second nasal passages, respectively. The width of each end region is preferably greater than the width of respective portions or components of resilient member 22 extending horizontally therein. End regions 32 and 34 include lateral end edges, 33a and 33b, respectively, which define the outer, lateral ends of truss 30 and thus dilator 10. End edges 33a and 33b may be angled inward in a straight line between upper and lower corners of the long edges of dilator 10, said angle corresponding approximately to the line where the nose meets the cheek. The width of intermediate region 36 is preferably narrower than the width of end regions 32 and 34, preferably without resilient member 22 being formed narrower at its mid section that at its outer ends as a result.

Finished dilators 10 are typically die cut from a continuous laminate of material layers. However, dilator layers, members or components thereof, material separations or horizontal regions of truss 30 may be formed or die cut, in whole or part, from one or more of continuous materials before, or during, assembly of the material laminate from which finished dilators 10 are die cut. In fabricating dilators 10, end regions 32 and 34 are preferably formed as mirror images of each other. However, asymmetric or non-identical end region configurations have the advantage of providing disparate dilating forces and tissue engaging surface areas to opposing nasal outer wall tissues, and thus more accurate or customized dilation or stabilization to the respective nasal passages. It will thus be obvious to the skilled man that virtually any two end region structures of the preferred embodiments herein may be intentionally combined in a given dilator device. For the sake of clarity and simplicity, however, the preferred embodiments illustrate end regions 32 and 34 as mirror images of each other. Additionally, certain of the enlarged fragmentary plan views refer to features of end region 34, but are equally applicable to end region 32.

When engaged to and flexed across a nose 11, dilator 10, through its resilient means as a result of its constituent members and layers combined to form single body truss 30, acts to stabilize and/or expand the nasal outer wall tissues and prevent said tissues from drawing inward during breathing.

Dilator 10 includes resilient means having resilient properties provided through its resilient layer and configured to provide suitable spring return biasing force as described hereinbefore. Overall spring biasing force is generally determined by the width, length, and thickness of at least one resilient member 22 or the resilient layer as a whole from its constituent member(s) and/or components. Resilient member 22 preferably has an adhesive substance disposed on at least a portion of at least one of two opposite flat surface sides for engaging or laminating it to other layers, members or components of dilator 10 or for engaging the skin surface of the nose. Resilient member 22 has opposite terminal ends, 23a and 23b, respectively, that may conform to at least portions of the lateral end edges 33a and 33b of dilator 10. Terminal ends 23a and 23b may extend to one or both of said lateral end edges of dilator 10, or may extend short of one or both end edges.

Dilator 10 includes means to direct its resilient properties. Said means may comprise configuration of, or modification to, the resilient layer or the material from which the resilient layer is formed. Said configuration or modification may be made either in the course of forming resilient member 22, or may be made to the resilient layer material separately, or at the time said material is assembled into the continuous material laminate from which dilator 10 is die cut (i.e., at the time the vertical laminate of dilator 10 is formed). Said configuration or modification may include cuts, notches, openings, or the like formed in the resilient layer material; or by varying the finished dimensions of the resilient member or a component thereof, such as by forming a gradiently tapered width; or by peripheral shape of the resilient member, such as by extensions or divergent spring finger components extending outward from its longitudinal extent; or by more than one resilient member, each member contributing a portion of the total spring biasing force. Having divergent spring fingers or multiple resilient members may increase the effective surface area subject to resilient layer spring biasing forces by spreading those forces to a greater, primarily lateral, surface area of dilator 10.

Said means to direct the resilient properties of dilator 10 further comprises at least one separation or discontinuity of shape of material of one or more regions or layers of truss 30. Said material separation or discontinuity of shape comprises a relief cut or back cut, slit, opening, notch, or the like, having a lateral and/or longitudinal extent, formed within the peripheral edges of dilator 10 (an interior material separation), or extending inward from a peripheral edge thereof (an exterior material separation). Said material separation extends vertically through at least one layer of dilator 10 and may optionally extend through release liner 15. An interior material separation extending across the width of the resilient member 22 redefines its functional length (said function being the creation of spring biasing forces when flexed), and thus changes the dimensional relationship between its length and width/thickness. This also changes the spatial, dimensional relationship between the functional portion of the resilient layer and the other members or layers of dilator 10. Said interior material separation thus further creates and defines at least one additional, substantially nonfunctional, component of the resilient layer.

One or more opposing pairs of interior or exterior material separations may be placed within or near respective end regions 32 and 34 of truss 30. An opposing pair is preferably positioned in a spaced apart relationship along or near the dilator's longitudinal centerline. The spacing apart of a pair of material separations is dynamic, and determines, at least in part, some degree of direction of resilient properties, as well as the longitudinal extent of dilator 10 affected thereby. Said means to direct resilient properties thus further comprises a dynamic relationship between the effect of an opposing pair of material separations and any other modification to, or configuration of, the resilient layer, including additional material separations or pairs thereof. For the sake of clarity and simplicity, interior and exterior material separations are shown uniform or as mirror images of each other in the preferred embodiments illustrated herein. As previously noted, however, asymmetric or non-identical elemental configurations have the advantage of providing disparate dilating forces and tissue engaging surface areas to opposing nasal outer wall tissues, and thus more accurate or customized dilation or stabilization to the respective nasal passages. Accordingly, it will be obvious to the skilled man that disparate material separations may be intentionally combined in a given dilator device, or identical or opposing material separations may be of dissimilar size or scale. Additionally, certain of the enlarged fragmentary plan views illustrate material separations positioned at end region 34, but are equally applicable to end region 32.

As detailed hereinbefore, an interior material separation extending vertically through dilator 10 including the resilient layer, may be contained entirely within the peripheral edges of resilient member 22 (or a component thereof) or extend inward from a peripheral edge thereof. Said material separation may allow formation of a flap capable of separating or vertically protruding, in part, from the resilient layer. Said separation or vertical protrusion may also change, at least in part, the angle of spring biasing forces of resilient member 22, while also allowing spring biasing forces to continue along a further extent of the resilient member or component. By virtue of extending vertically through the resilient member without severing its entire width, said interior material separation reduces the total spring biasing force of resilient member 22, primarily from the point of said separation to the adjacent terminal end thereof. In this manner, an opposing pair of interior material separations may be spaced apart along the horizontal extent of resilient member 22 so as to redirect a greater portion of total spring biasing force between the spaced apart pair and a corresponding lesser portion extending from each separation to corresponding terminal ends 23a and 23b.

Accordingly, the type, number, and location of one or more interior and/or material separations or pairs thereof, the configuration of resilient member 22 and its corresponding resiliency, the relative size and shape of end regions 32 and 34, and the dynamic relationships between these various elements, all contribute to directing the resilient properties of dilator 10. Various examples thereof are given in the preferred embodiments and discussed in more detail herein below.

Figure 4:
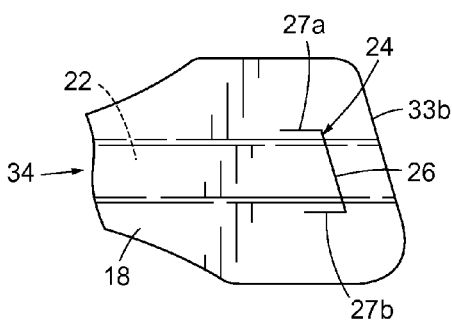
FIG. 4 is a fragmentary plan view, on an enlarged scale, illustrating one end region of the nasal dilator of FIG. 3.
Figure 3:
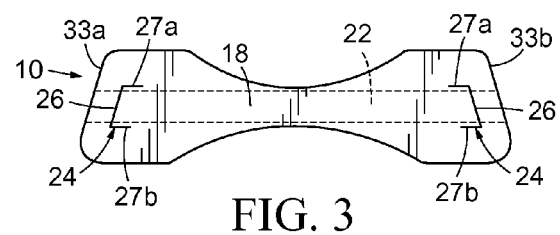
FIG. 3 is a plan view of the nasal dilator of FIG. 1.

As seen in FIGS. 1-15, an interior material separation comprises a relief cut, 24, located within each end region of truss 30. Relief cut 24 preferably extends vertically through the cover, resilient and base layers of dilator 10. FIG. 4 more particularly identifies relief cut 24 having an outside edge, 26, which defines its width, and upper and lower long edges, 27a and 27b which define at least portions of its length. Outside edge 26 preferably corresponds to at least a portion of the nearest end edge 33a or 33b, respectively, of end regions 32 and 34. (As discussed hereinbefore, each end region is shown as a mirror image of the other, so only one end region will be described with particularity.). Outside edge 26 severs the entire width of resilient member 22 laterally, preferably extending slightly past the upper and lower long edges thereof, before turning to upper and lower edges 27a and 27b. Upper and lower edges 27a and 27b extend inward preferably about 0.125" in a direction parallel to upper and lower long edges of resilient member 22. Relief cuts 24 redefine the functional length of resilient member 22, as described hereinbefore, creating additional, substantially nonfunctional, resilient layer components.

Figure 5:
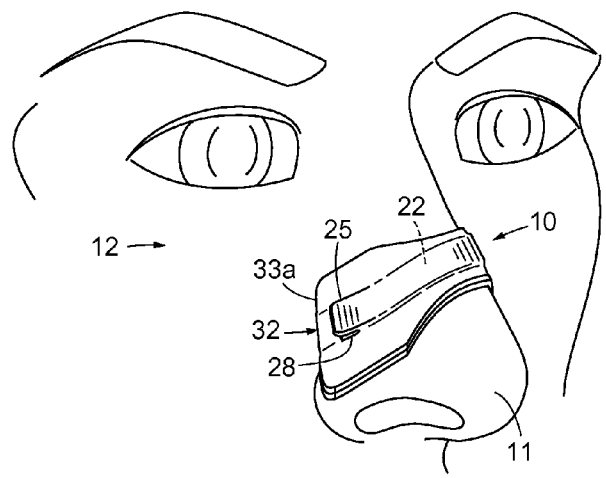
FIG. 5 is a perspective view of a portion of a face with the nasal dilator of FIG. 1. secured to the nose.
Figure 6:
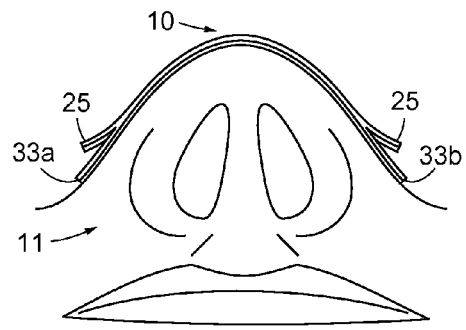
FIG. 6 is a front elevation view of the nasal dilator of FIG. 5 secured to the nose, seen as a portion of a face, of a wearer.
Figure 7:
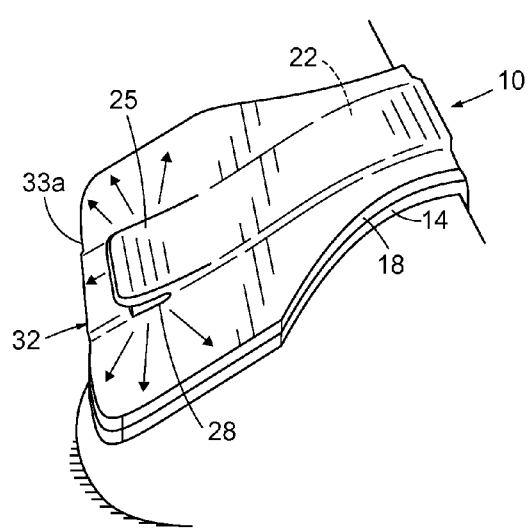
FIG. 7 is a is a fragmentary perspective view, on an enlarged scale, of the dilator of FIG. 5 secured to the nose of a wearer.

FIGS. 5-7 show dilator 10 adhered to and flexed across the bridge of a nose, 11, seen as a portion of a human face, 12. Relief cut 24 allows formation of a flap, 25, at the redefined terminal ends of resilient member 22, said flap capable of separating or vertically protruding, in part, from respective end regions 32 and 34 of truss 30, and leaving a corresponding opening or gap, 28, from where it separates from the truss when dilator 10 is engaged to nose 11. The length of upper and lower edges 27a and 27b and the width of outside edge 26 of relief cut 24 define the shape and dimensions of flap 25; its length being parallel to the longitudinal extent of resilient member 22. Said length determines in part the degree of said separation or vertical protrusion and the corresponding change in angle, and thus transfer, of focused spring biasing forces from primarily peel forces and tensile forces into primarily shear forces, as discussed hereinbefore. Said transformed spring biasing forces are redistributed or imparted to tissue engaging surfaces of dilator 10 extending in an area between gap 28 and the surrounding peripheral edges of end region 32, as generally illustrated by directional arrows in FIG. 7. Relief cuts 24 are preferably spaced apart along the longitudinal extent of dilator 10, placed closer to respective end edges 33a and 33b than to intermediate region 36, so as to direct resilient properties along a greater, rather than lesser, longitudinal extent of dilator 10.

Figure 8:
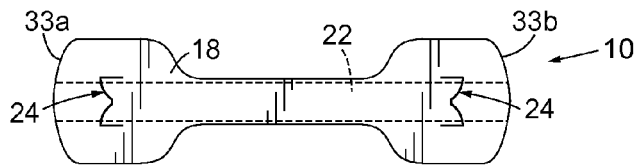
FIG. 8 is a plan view of a variation of the nasal dilator of FIG. 1.
Figure 9:
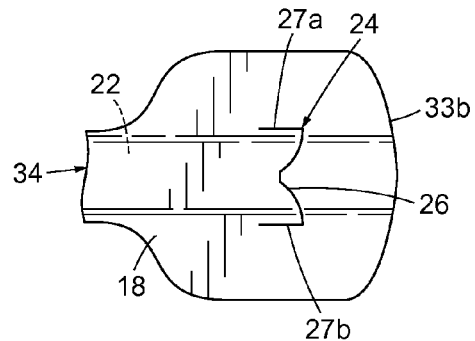
FIG. 9 is a fragmentary plan view, on an enlarged scale, illustrating one end region of the nasal dilator of FIG. 8.

FIGS. 8-9 illustrate a variation of the nasal dilator of FIG. 1 in which relief cut 24 has a scalloped edge. FIG. 9 shows outside edge 26 extending from respective upper and lower edges 27a and 27b, intersecting upper and lower long edges of resilient member 22 at substantially right angles thereto, before curving arcuately inward to form two scalloped portions of identical length and width. The respective lengths of said scalloped portions may be defined by the respective lengths of upper and lower edges 27a and 27b and by the horizontal location of the intersection between each scalloped portion. As more particularly illustrated in FIG. 9, portions of end edge 33b curve arcuately between upper and lower long edges of end region 34. The apex of said arcuate curve preferably corresponds to the longitudinal axis of dilator 10. Terminal end 23b of resilient member 22 terminates along said apex. End edge 33b may optionally correspond to the scalloped contour of outside edge 26.

Figure 10:
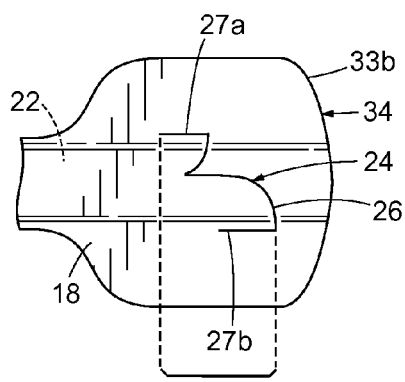
FIG. 10 is a fragmentary plan view, on an enlarged scale, illustrating an alternative end region structure to that of the nasal dilator of FIG. 9.

FIG. 10 shows an alternative structure of relief cut 24 illustrated in FIG. 9 in which outside edge 26 forms scalloped portions of dissimilar shape. FIG. 10 indicates by bracketed broken lines the total length of relief cut 24 being defined by the respective lengths of upper and lower edges 27a and 27b and the contour of outside edge 26. The respective widths of scalloped portions thereof may be either identical or dissimilar, and are defined by the location of the intersection therebetween. The length and width of the scalloped portions of outside edge 26 of relief cut 24 may result in slightly greater spring biasing forces imparted along the upper long edge of resilient member 22. In addition, the longer of the two scalloped portions tend to cause greater separation of flap 25 from gap 28, thus having a corresponding effect on spring biasing properties of dilator 10 as discussed hereinbefore.

Figure 12:
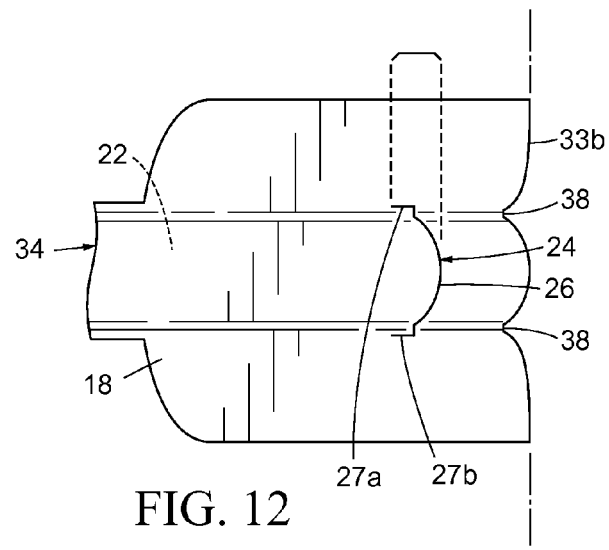
FIG. 12 is a fragmentary plan view, on an enlarged scale, illustrating one end region of the nasal dilator of FIG. 11.
Figure 11:
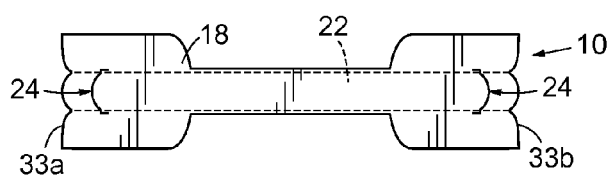
FIG. 11 is a plan view of an alternative form of nasal dilator embodying features of the present invention.

FIGS. 11-12 illustrates another alternative structure of relief cut 24 in which outside edge 26 forms a scalloped edge identical to a portion of corresponding end edge 33b or 33b. As more particularly illustrated in FIG. 12, outside edge 26 of relief cut 24 extends from upper and lower edges 27a and 27b, preferably intersecting upper and lower long edges of resilient member 22 at right angles thereto before forming a single scalloped edge. Said scalloped edge conforms to a corresponding center portion of end edge 33b of end region 34. The total length of relief cut 24, denoted by bracketed broken lines, is defined by the length of upper and lower edges 27a and 27b, plus the horizontal extent of the scalloped portion of outside edge 26 extending toward end edge 33b.

FIG. 12 further illustrates end edge 33b having three portions situated along a common lateral plane, represented by broken lines. Said lateral plane may be optionally set at an oblique angle to the long axis of dilator 10, corresponding approximately to the line where nose 11 meets the cheek of a face 12. The upper and lower of said three portions curve arcuately inward from the outside corners of upper and lower long edges of end region 34, forming an exterior material separation comprising a valley, 38, at the intersections of respective upper and lower corners of terminal end 23b of resilient member 22. From the intersections formed by valleys 38, end edge 33b curves outwardly again to form said scalloped center portion. The apex of said center portion corresponds to the longitudinal axis of resilient member 22, with terminal end 23b thereof terminating along said scalloped center portion.

Figure 14:
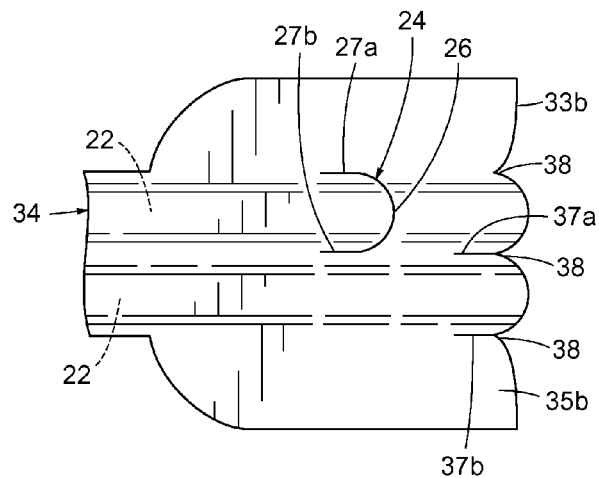
FIG. 14 is a fragmentary plan view, on an enlarged scale, illustrating one end region of the nasal dilator of FIG. 13.
Figure 13:
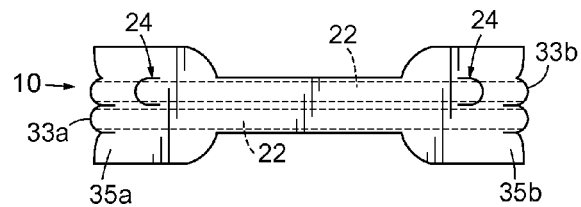
FIG. 13 is a plan view of an alternative form of nasal dilator embodying features of the present invention.

FIGS. 13-14 illustrate a combination of interior and exterior material separations in accordance with the present invention. FIG. 13 shows end edges 33a and 33b having scalloped portions which correspond substantially to terminal ends 23a and 23b of a pair of parallel, spaced apart, resilient members 22. Said terminal ends define the longitudinal extent of dilator 10. A pair of interior material separations comprising relief cuts 24 are placed in a spaced apart relationship in opposing end regions of truss 30, each relief cut forming a scalloped edge across the width of at least one of said pair of resilient members 22. FIG. 14 more particularly shows outside edge 26 of relief cut 24 intersecting upper and lower long edges 27a and 27b, respectively, at oblique angles thereto. The shape of outside edge 26 preferably corresponds to a corresponding portion of scalloped end edge 33b.

FIG. 14 further illustrates a pair of exterior material separations comprising upper and lower back cuts, 37a and 37b, extending vertically through at least the cover layer of dilator 10 and inward from end edge 33b. Each back cut is positioned at the intersection of a corresponding valley 38, adjacent and parallel to the upper and lower long edges of at least one resilient member 22. This arrangement defines a horizontal protrusion at the end portions of said one resilient member. Lower back cut 37b forms a separation between said horizontal protrusion and a corresponding lower extension, 35b. Extension 35b may optionally extend horizontally beyond terminal end 23b, and thus may further define the longitudinal extent of dilator 10.

The interior material separation positioned in end region 34 may allow formation of a flap 25 at the redefined terminal ends of upper resilient member 22, capable of separating or vertically protruding, in part, from truss 30 when dilator 10 is flexed across the nose. Similarly, the horizontal protrusion defined by upper and lower back cuts 37a and 37b is also capable of separating or protruding vertically, in part, from the truss when the dilator is flexed across the nose of a wearer. In each case the material separation changes the angle, in part, of focused spring biasing forces, transforming said forces as described hereinbefore. With respect to the interior material separation, said transformed forces are imparted to the end region in general. With respect to said exterior material separations, said transformed forces are imparted, at least in part, to extension 35b.

The parallel spaced apart resilient members 22 may be of like or dissimilar width. A dynamic relationship exists not only between the respective spring biasing properties of multiple resilient members of dissimilar widths, but also between the location of relief cuts 24, the length(s) of relief cut(s) 24, back cuts 37*a* and 37*b*, and the combined spring biasing forces generated by said pair of resilient members 22. Though all of these elements are shown as symmetric pairs, it will be obvious to the skilled man that said elements may be resized, recombined or omitted.

Figure 15:
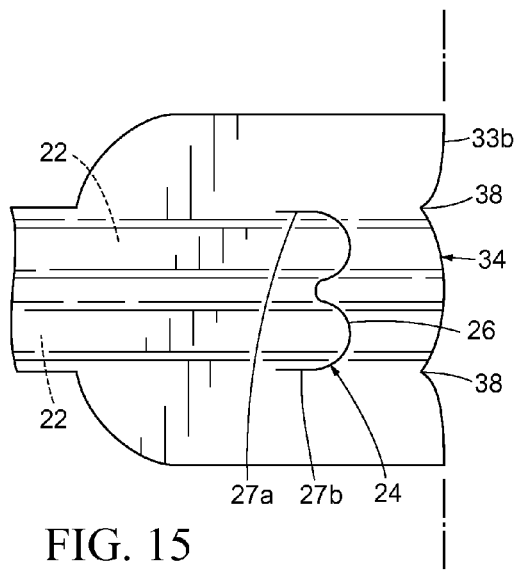
FIG. 15 is a fragmentary plan view, on an enlarged scale, illustrating an alternative end region structure to that of the nasal dilator of FIG. 14.

FIG. 15 illustrates an alternative end region structure to that shown in the embodiment of FIG. 14, in which relief cut 24 extends across said pair of resilient members 22. Respective scalloped portions of outside edge 26 extend across the width of each resilient member. End edge 33*b* has three portions situated along a common lateral plane. Said plane is shown perpendicular to the long axis of dilator 10, but may be optionally situated at an oblique angle thereto, corresponding approximately to the line where the nose meets the cheek. The upper and lower of said three portions curve arcuately inward from the outside corners of upper and lower long edges of end region 34, forming valley 38 at intersections adjacent above and below respective upper and lower corners of terminal ends 23*b* of said pair of resilient members 22. From said intersections end edge 33*b* curves outwardly again to form said scalloped center portion. The apex of said center portion corresponds to the longitudinal axis of the pair of resilient members 22, with terminal ends 23*b* thereof terminating along said scalloped center portion.

Figure 16:
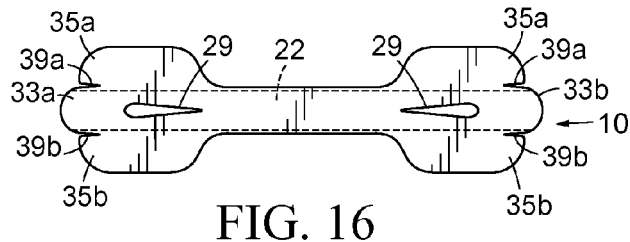
FIG. 16 is a plan view of an alternative form of nasal dilator embodying features of the present invention.
Figure 17:
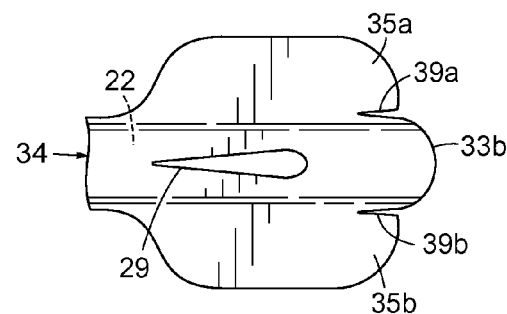
FIG. 17 is a fragmentary plan view, on an enlarged scale, illustrating one end region of the nasal dilator of FIG. 16.

FIGS. 16-17 illustrate another combination of interior and exterior material separations in accordance with the present invention. End edges 33*a* and 33*b* form a scalloped portion corresponding to respective terminal ends 23*a* and 23*b* of resilient member 22. The distance between said terminal ends represents the longitudinal extent of dilator 10. Exterior material separations comprising upper and lower notches, 39*a* and 39*b*, are positioned parallel to and adjacent upper and lower long edges of resilient member 22. Notches 39*a* and 39*b* extend vertically through the base and cover layers of dilator 10, and inward from end edges 33*a* and 33*b*, respectively. Notches 39*a* and 39*b* define intersections between said scalloped portion of end edges 33*a* and 33*b* and upper and lower tab extensions 35*a* and 35*b*, respectively, of end regions 32 and 34. Tab extensions 35*a* and 35*b* may optionally extend to, or beyond, said scalloped portions, the latter thus further defining the longitudinal extent of dilator 10. As more particularly illustrated in FIG. 17, said scalloped mid portion of end edge 33*b* and notches 39*a* and 39*b* define a horizontal protrusion, also capable of separating in part from the end region 34, as discussed hereinbefore. Said separation changes the angle, at least in part, of spring biasing forces, and shifts and transforms said forces, similarly as described with respect to FIG. 13, imparting said transformed forces to both upper and lower tab extensions 35*a* and 35*b* of end region 34.

The dilator of FIGS. 16-17 further includes an opposing pair of interior material separations each comprising an elongated opening, 29, extending vertically through at least resilient member 22 and contained within the width thereof. Opening 29 may be optionally formed before assembly of the vertical laminate of dilator 10, or (as shown) formed as dilator 10 is die cut from a continuous material laminate. Opening 29 has a gradient increase in width along its length, extending horizontally from inward to outward, which defines corresponding adjacent upper and lower portions of resilient member 22 having a gradient reduction in width. Opening 29 may be of any size or shape contained within the width of resilient member 22. Each of the opposing pair thereof is preferably positioned horizontally between the lateral centerline of truss 30 and respective end edges 33*a* and 33*b*.

The relative width of opening 29 compared to the width of resilient member 22 thereat, together with the distance between said opposing pair of openings 29 defines a dynamic relationship, which determines spring biasing forces generated between said openings and extending beyond each opening to corresponding terminal ends 23*a* and 23*b*, respectively, of resilient member 22. Another dynamic relationship exists between the configuration of interior material separations, openings 29, and the exterior material separations at respective end edges 33*a* and 33*b*.

Figure 18:
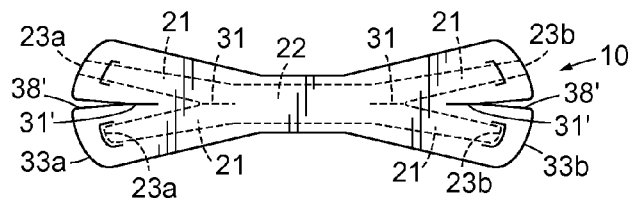
FIG. 18 is a plan view of an alternative form of nasal dilator embodying features of the present invention.
Figure 19:
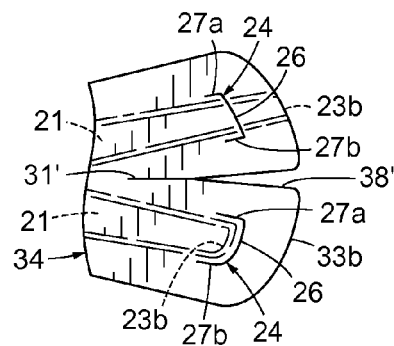
FIG. 19 is a fragmentary plan view, on an enlarged scale, illustrating a portion of one end region of the nasal dilator of FIG. 18.

FIGS. 18-19 illustrate an embodiment of dilator 10 in accordance with the present invention in which the end regions of truss 30 include upper and lower bifurcated end region portions. In addition, resilient member 22 includes a plurality of component spring fingers, 21, diverging and extending outward from a common center. Said common center is preferably aligned with the lateral and longitudinal centerlines of intermediate region 36. Spring biasing forces generated by the resilient layer of dilator 10 are gradiently reduced, at least in part, in the course of being directed to spring fingers 21. Upper and lower fingers 21 having uniform gradient widths, but may optionally curve, be asymmetric, and may be equidistant or of varying distance from said common center. As noted hereinbefore, divergent or asymmetric dilator features can provide disparate spring biasing forces. Fingers 21 may be further defined by a slit, 31, extending inward from the point where upper fingers diverge from lower fingers.

Fingers 21 extend into corresponding bifurcated portions of end regions 32 and 34. Terminal ends 23*a* and 23*b* of upper fingers 21 extend to, and conform with, portions of end edges 33*a* and 33*b* thereat. Terminal ends 23*a* and 23*b* of lower fingers 21 extend short of end edges 33*a* and 33*b*. Spring fingers 21 and slits 31 of resilient member 22 are configurations preferably made prior to assembling the vertical laminate of dilator 10. The divergent extent of spring fingers 21 determines the lateral spread of spring biasing forces at end regions 32 and 34. The gradient width and the length of each spring finger 21, defined in part by the length of slit 31, determines the gradient reduction in spring biasing forces along the longitudinal and lateral extents of resilient member 22. In addition, the divergent end region structure of dilator 10 provides additional lateral, torsional, flexibility primarily at the end regions, allowing dilator 10 to simultaneously effect dilation of nasal outer wall tissues adjacent both the nasal valve and nasal vestibule.

As more particularly illustrated in FIG. 19, end edge 33*b* has one of two exterior material separations comprising a valley, 38', forming the intersection between said upper and lower bifurcated end region portions. A second exterior material separation comprising a slit, 31', extends inward from the terminus of valley 38' preferably along the longitudinal axis of truss 30, corresponding to slit 31 in resilient member 22. Slit 31' preferably extends short of resilient member 22.

As further illustrated in FIG. 19, upper bifurcated end region portions include relief cut 24 extending across the width of upper spring finger 21. Another relief cut 24 is positioned outboard and adjacent terminal end 23*b* of lower spring finger 21, corresponding to the shape of said terminal end. Relief cuts 24 have upper and lower edges 27*a* and 27*b*, respectively, defining their length and extending parallel to the long edges of spring finger 21. Outside edge 26 preferably extends beyond upper and lower long edges of spring finger 21, substantially following the contour of the corresponding end edge 33*b*. Relief cuts 24 allow formation of a flap, as described hereinbefore, capable of separating or vertically protruding, in part, when dilator 10 is flexed across the nose; said separations or vertical protrusions changing the angle, in part, of spring biasing forces, as described hereinbefore, transforming said forces and imparting them, at least in part, to tissue engaging surface areas extending outward to corresponding peripheral edges of said bifurcated end region portions of truss 30.

Figure 20:
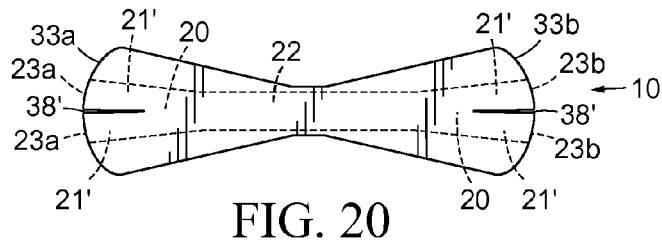
FIG. 20 is a plan view of an alternative form of nasal dilator embodying features of the present invention.
Figure 21:
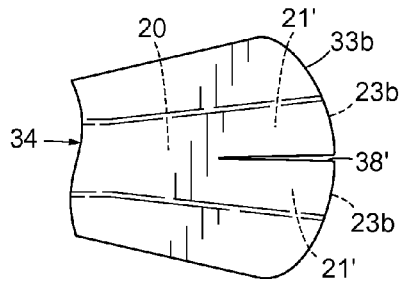
FIG. 21 is a fragmentary plan view, on an enlarged scale, illustrating a portion of one end region of the nasal dilator of FIG. 20.

FIGS. 20-21 illustrate an embodiment in accordance with the present invention where enlarged end portions, 20, of resilient member 22, formed as a modification prior to assembling the vertical laminate of dilator 10, correspond generally to the shape of end regions 32 and 34 of truss 30. Resilient member end edges 23a and 23b extend to, and conform with, portions of end region end edges 33a and 33b, respectively. As more particularly illustrated in FIG. 21, valley 38' extends inward from said end edge, simultaneously bifurcating end regions 32 and 34, as well as enlarged end portions, 20, of resilient member 22. Said bifurcation forms spring fingers, 21', in resilient member 22 and upper/lower bifurcated end region portions having common inside long edges therewith. Valley 38' may be configured to gradiently reduce the width of at least one spring finger 21'. Depending upon the dimensional relationship between the width of enlarged end portions 20 and the length and width of valley 38', said bifurcation may laterally spread, and/or reduce, or gradiently reduce the spring biasing forces of dilator 10 primarily at end regions 32 and 34. This divergent end region structure provides additional lateral torsional flexibility primarily at the end regions of truss 30, allowing dilator 10 to simultaneously effect dilation of nasal outer wall tissues adjacent both the nasal valve and nasal vestibule.

Figure 22:
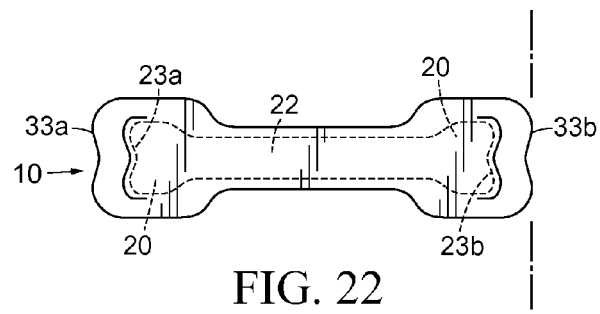
FIG. 22 is a plan view of an alternative form of nasal dilator embodying features of the present invention.
Figure 23:
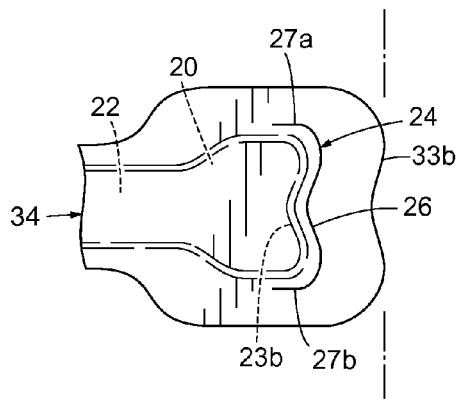
FIG. 23 is a fragmentary plan view, on an enlarged scale, illustrating one end region of the nasal dilator of FIG. 22.

FIGS. 22-23 illustrate an embodiment of dilator 10 in accordance with the present invention in which enlarged end portions 20 of resilient member 22 correspond substantially to the peripheral shape of the respective end regions of truss 30 and are positioned substantially at the lateral and longitudinal axes thereof. Resilient member terminal ends 23a and 23b thus extend short of, but conform with, end region end edges 33a and 33b, respectively, of said end regions. Said end edges form upper and lower horizontal protrusions extending to a common lateral plane, represented by broken lines, perpendicular to the long axis of dilator 10. Said horizontal protrusions define the longitudinal extent of dilator 10.

As more particularly illustrated in FIG. 23, relief cut 24 is positioned adjacent terminal end 23b of resilient member 22, preferably as closely as practicable thereto. Its upper and lower edges 27a and 27b extend parallel to, and at least partway along, upper and lower long edges of enlarged end portions 20. Outside edge 26 corresponds generally to the contour of terminal end 23b of resilient member 22. The width of enlarged end portion 20 spreads spring biasing forces generated by resilient member 22, at least in part, laterally across end region 34. Relief cut 24 may cause the terminal end of resilient member 22 to separate or vertically protrude from the truss when dilator 10 is flexed across the nose, with the corresponding effect thereat as described hereinbefore, transforming said forces and imparting them, at least in part, to tissue engaging surface areas extending outward and beyond relief cut 24 to corresponding peripheral edges of end region 34.

Figure 25:
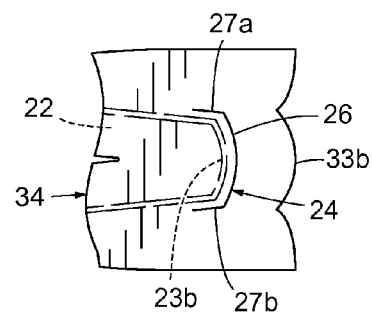
FIG. 25 is a fragmentary plan view, on an enlarged scale, illustrating a portion of one end region of the nasal dilator of FIG. 24.
Figure 24:
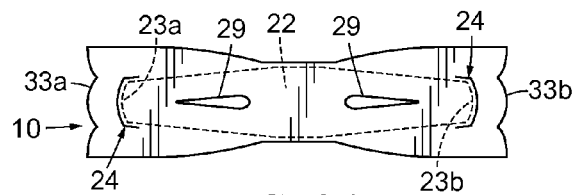
FIG. 24 is a plan view of an alternative form of nasal dilator embodying features of the present invention.

FIGS. 24-34 illustrate variations of an embodiment of dilator 10 in accordance with the present invention in which resilient member 22 has a gradiently reduced width which provides reduced spring biasing force extending horizontally from the lateral centerline of truss 30 to respective terminal ends 23a and 23b. The mid portion of resilient member 22 preferably has a constant width representing its widest portion. In the embodiment of FIGS. 24 and 25, terminal ends 23a and 23b extend short of respective lateral end edges 33a and 33b of truss 30. In the embodiment of FIGS. 26-34, said terminal ends extend to, and conform with, portions of said respective lateral end edges.

The embodiment of dilator 10 shown in FIGS. 24-25 shows relief cut 24 placed outboard and adjacent terminal ends 23a and 23b of resilient member 22. Relief cut 24 extends around and corresponds to the periphery of each said terminal end, substantially as described with respect to the embodiment of FIGS. 22 and 23. As described hereinbefore, relief cut 24 may cause the terminal end of resilient member 22 to separate or vertically protrude from the truss when dilator 10 is flexed across the nose, with the corresponding effect thereat as described hereinbefore, transforming said forces and imparting them, at least in part, to tissue engaging surface areas extending outward and beyond relief cut 24 to corresponding peripheral edges of end region 34.

As further illustrated in FIG. 24, dilator 10 includes two elongated openings 29 extending vertically through at least the resilient layer, similar to that described with respect to openings 29 in the embodiment of FIGS. 16 and 17. Opening 29 is horizontally positioned at the approximate intersection of intermediate region 36 and respective end regions 32 and 34 of truss 30. In this instance, opening 29 has its widest end placed to the inside, with upper and lower long edges parallel to the upper and lower long edges of resilient member 22. Opening 29 thus defines upper and lower portions of resilient member 22 adjacent thereto having a constant width. The closed end of opening 29 may optionally include a slit extending to corresponding terminal end 23a or 23b of resilient member 22.

Figure 26:
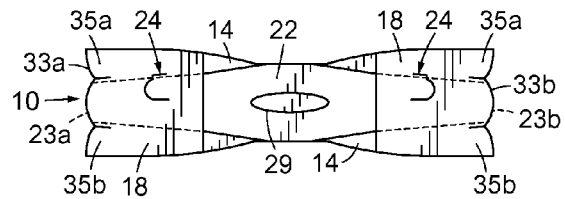
FIG. 26 is a plan view of an alternative form of nasal dilator embodying features of the present invention.
Figure 27:
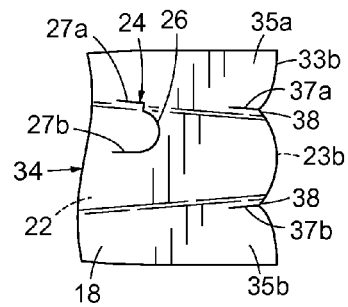
FIG. 27 is a fragmentary plan view, on an enlarged scale, illustrating a portion of one end region of the nasal dilator of FIG. 26.
Figure 28:
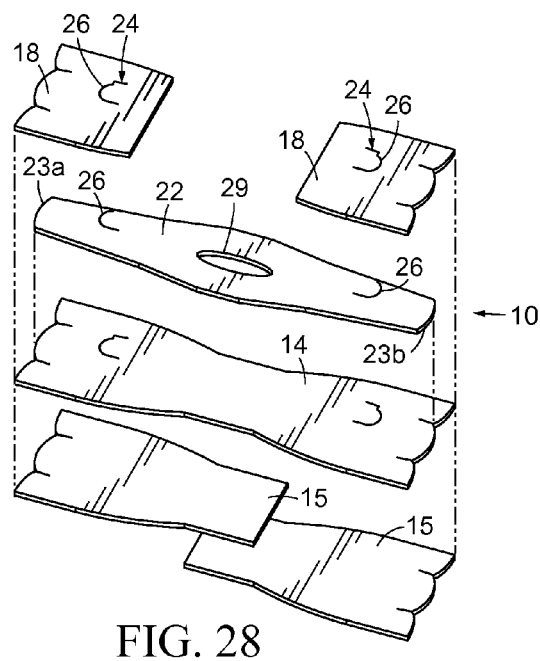
FIG. 28 is an exploded perspective view of the nasal dilator of FIG. 26.

FIGS. 26-28 illustrate an alternative structure in which the resilient and base layers of dilator 10 converge toward common upper and lower long edges at intermediate region 36. Two opposing relief cuts 24 extend vertically through the truss, including the resilient layer thereof, severing a portion of the width of resilient member 22. Cover member 18 comprises two components each corresponding substantially to respective end regions 32 and 34 of truss 30, thus leaving portions of the resilient and base layers uncovered. A single interior material separation comprising elongated opening 29 is positioned at the lateral and longitudinal centerlines of the truss, extending vertically at least through resilient member 22. Opening 29 also serves as an aid for aligning dilator 10 to the bridge of nose 11. The peripheral shape of resilient member 22 and opening 29 may be formed prior to assembling the constituent layers of dilator 10.

Opening 29 effectively reduces the spring biasing strength of resilient from that which would otherwise be generated at its widest portion. Accordingly, there is a dynamic relationship between the size of opening 29 and the dimensions of resilient member 22, said dynamic relationship contributing to the direction of spring biasing properties of dilator 10. Opening 29 and relief cuts 24 direct spring biasing properties extending outward horizontally from intermediate region 36 when dilator 10 is in use on nose 11. Relief cut 24 includes a scalloped outside edge 26 which allows formation of a partial flap capable of separating or vertically protruding, in part, from resilient member 22 when the dilator is flexed across the nose of a wearer. The degree of vertical protrusion thereat is limited, however, the dynamic relationship between the size, shape and position of opposing relief cuts 24, relative to the dimensions of resilient member 22, determine the distribution of focused spring biasing forces therebetween, as well as those forces extending beyond each relief cut 24 toward respective terminal ends 23a and 23b when dilator 10 is in use on nose 11. Said terminal ends extend to, and conform with, a scalloped mid portion of end edges 33a and 33b of truss 30.

As more particularly illustrated in FIG. 27, upper edge 27a of relief cut 24 extends parallel to upper long edge of resilient member 22. Outside edge 26 intersects the upper long edge of resilient member 22 at a right angle thereto before curving arcuately outward to form scalloped edge 26. The mid portion of end edge 33b is defined by upper and lower back cuts 37a and 37b, positioned adjacent upper and lower long edges of resilient member 22. Back cuts 37a and 37b extend vertically through the base and cover layers and inward from corresponding valley 38 at end edge 33b, similarly as described with respect to the embodiments of FIGS. 13-14 and 16-17. Together with back cuts 37a and 37b, said scalloped mid portion of end edge 33b defines a horizontal protrusion, also capable of separating in part from end region 34. Said separation changes the angle, at least in part, of spring biasing forces extending beyond relief cuts 24, and shifts and transforms said forces, as described hereinbefore, redistributing said transformed forces, at least in part, to upper and lower tab extensions 35a and 35b.

Figure 29:
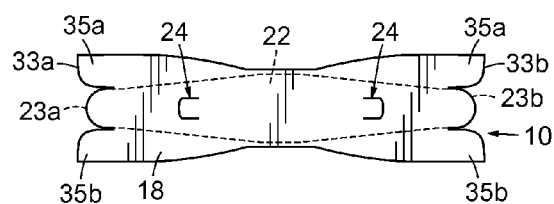
FIG. 29 is a plan view of an alternative form of nasal dilator embodying features of the present invention.

FIGS. 29-32 illustrate another alternative structure of dilator 10 in which opposing pairs of interior and exterior material separations, together with the configuration of the resilient layer, direct the resilient properties of dilator 10. FIG. 29 shows interior material separations comprising opposing relief cuts 24 extending vertically through dilator 10. Relief cuts 24 are positioned at opposite ends of the intermediate region of truss 30 substantially at the intersections between intermediate region 36 and respective end regions 32 and 34 thereof. Relief cuts 24 each form a flap capable of separating or vertically protruding, in part, from the resilient layer when the dilator is flexed across the nose, and may be any size contained within the peripheral edges of resilient member 22, with the corresponding effect thereat as described hereinbefore. The relative sizes of opposing relief cuts 24 together with the gradiently reduced width of resilient member 22 contribute to the overall gradient reduction of spring biasing properties of the resilient layer extending horizontally from intermediate region 36 to respective end regions 32 and 34. Depending upon the lateral extend of outside edge 26 and the length of upper and lower long edges 27a and 27b, opposing relief cuts 24 may also dynamically direct a greater amount of total spring biasing force to the horizontal extent therebetween and a lesser amount extending beyond each relief cut 24 to respective end edges of truss 30.

Figure 30:
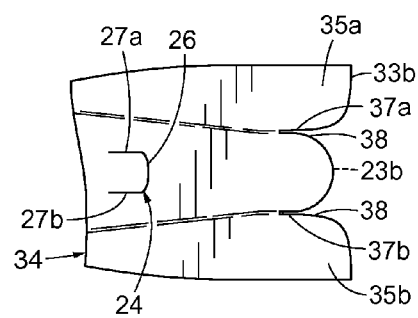
FIG. 30 is a fragmentary plan view, on an enlarged scale, illustrating a portion of one end region of the nasal dilator of FIG. 29.
Figure 31:
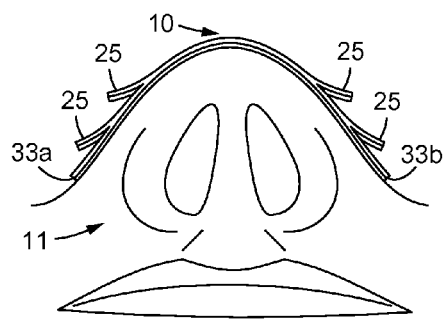
FIG. 31 is a front elevation view of the nasal dilator of FIG. 29 secured to a nose, seen as a portion of a face, of a wearer.

FIG. 30 more particularly illustrates said exterior material separations comprising upper and lower back cuts 37a and 37b, extending inward from a corresponding valley 38 at end edge 33b adjacent upper and lower long edges of resilient member 22, as described hereinbefore. Together with back cuts 37a and 37b, the scalloped mid portion of end edge 33b defines a horizontal protrusion, also capable of separating in part from the end region 34 when dilator 10 is flexed across a nose 11, redistributing transformed spring biasing forces to tab extensions 35a and 35b of end region 34 as described hereinbefore. FIG. 31 more clearly illustrates separation flaps 25 formed by said interior and exterior material separations, separating or vertically protruding, in part, from end regions 32 and 34 of truss 30, directing resilient properties thereof as described hereinbefore.

Figure 32:
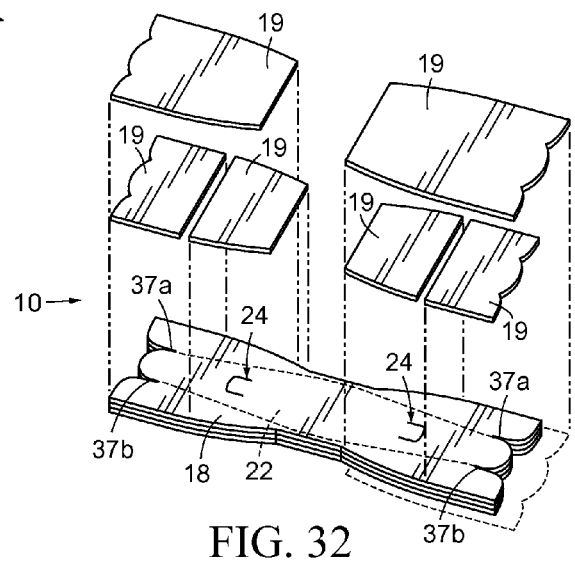
FIG. 32 is an exploded perspective view of the nasal dilator of FIG. 29 including additional end region components.

As illustrated in FIG. 32, dilator 10 includes means to prevent one or more material separations from separating or vertically protruding from the truss. An additional cover layer component, 19, may be optionally applied by a user over one or more of said interior or exterior material separations, effectively hindering or preventing at least a portion of its separation or vertical protrusion from truss 30. End region component 19 preferably corresponds in shape to at least a portion of either end region of truss 30, and may, for example, be peeled by hand from a sheet containing a plurality thereof (i.e., in the same manner one would peel a self-adhesive label from a continuous sheet thereof) and placed on top of a corresponding portion of cover member 18, preferably centered over one or more said material separation(s). Component 19 may also be configured such that its peripheral edges extend beyond the peripheral edges of said horizontal portion of cover member 18, as shown, effectively allowing the user to extend or increase the tissue engaging surface area of dilator 10. It will be obvious to the skilled man in the art that end region component 19 may be added to virtually any of the preferred embodiments illustrated herein.

Figure 33:
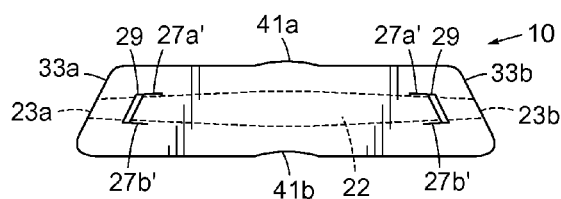
FIG. 33 is a plan view of an alternative form of nasal dilator embodying features of the present invention.
Figure 34:
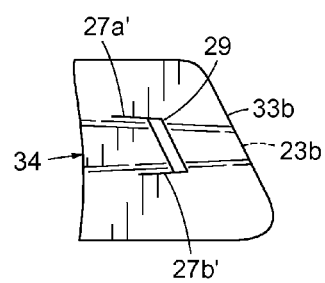
FIG. 34 is a fragmentary plan view, on an enlarged scale, illustrating a portion of one end region of the nasal dilator of FIG. 33.

FIGS. 33-34 illustrate an embodiment of dilator 10 in accordance with the present invention in which an opening and relief cuts are combined into a single element. Opening 29 extends vertically through and laterally across the upper and lower long edges of resilient member 22. The outside edge of opening 29 preferably conforms to corresponding end edge 33a or 33b of truss 30 which, in the present example, is angled inward in a straight line between upper and lower corners of the long edges of dilator 10, said angle corresponding approximately to the line where the nose meets the cheek. Opening 29 includes upper and lower relief cuts, 27a' and 27b', extending inward from the respective upper and lower inside corners thereof, adjacent and parallel to the upper and lower long edges of resilient member 22. Relief cuts 27a' and 27b' allow formation of a flap at the redefined terminal ends of resilient member 22, said flap capable of separating or vertically protruding, in part, from the truss when dilator 10 is flexed across the nose, with the corresponding effect thereat as described hereinbefore.

With respect to FIGS. 24-34, and as described hereinbefore, a dynamic relationship exists between the configuration of resilient member 22 (in these particular embodiments, the gradient tapering of its upper and lower long edges), and a combination of interior and exterior material separations, plus additional, optionally user-applied components, each and all contributing to the direction of resilient properties of dilator 10.

The dilator of FIGS. 33-34 further includes a material formation, 41a and 41b, located along the upper and lower long edges of intermediate region 36 midway between end edges 33a and 33b. Formation 41a comprises an upper protrusion and a corresponding lower indentation 41b. Material formation 21 may be of any suitable size or shape, and may be symmetric, asymmetric, straight, curved or gradient. Formation 41 forms a positioning aid for aligning dilator 10 to a nose 11. When dilator 10 is applied to the nose, one or more formations 41 are meant to be aligned with the vertical center line of the bridge of the nose by the user, thus aiding precise horizontal placement of dilator 10 to nose 11. Alternatively, one or more material formation 41 may be made within the periphery of truss 30, and need not extend through all layers thereof so long as they are visible, and allow the user to align the lateral center of dilator 10 with the vertical center line of the bridge of nose 11.

The foregoing descriptions and illustrations are intended to reveal the scope and spirit of the present invention and should not be interpreted as limiting, but rather as illustrative of the inventive concepts and techniques thereof. Skilled men in the art to which the present invention is directed will appreciate that insubstantial changes, modifications and alterations of the present disclosure may be made and each such insubstantial change, modification and alteration are intended to be fully covered hereby.

I claim:

1. A nasal dilator comprising a laminate of vertical layers including a resilient member laminated to at least one of a base layer or cover layer, said resilient member extending fully from lateral end edge to opposite lateral end edge of the dilator, said base layer or cover layer extending horizontally beyond said resilient member at a portion of a periphery of the dilator outboard of upper and lower long edges of the resilient member; and the dilator further including a symmetrical material separation extending vertically through every layer of the laminate, the material separation extending inward from each lateral end edge of the dilator, bifurcating the laminate so as to define upper and lower resilient member spring fingers and corresponding upper and lower bifurcated dilator end region portions, the resilient member and the base layer or cover layer thus having a common peripheral edge extending along at least a portion of the material separation.

2. The nasal dilator of claim 1 wherein the material separation comprises a valley having a predetermined length and width, the width being substantially constant along said length.

3. The nasal dilator of claim 1 wherein the material separation extends inward a predetermined distance from about 20% to about 40% of a longitudinal extent of the dilator.

4. The nasal dilator of claim 1 wherein said upper and lower spring fingers have similar length, width, and peripheral shape.

5. The nasal dilator of claim 1 wherein said, resilient member and said base layer or cover layer are formed from a plastic film material.

6. The nasal dilator of claim 1 wherein said base layer or cover layer is interposed between the resilient layer and skin surfaces of a nose when the dilator is in use thereon.

7. The nasal dilator of claim 1 wherein upper and lower long edges of the dilator are defined by said base layer or cover layer.

8. The nasal dilator of claim 1 wherein upper and lower long edges of the material separation are substantially parallel to upper and lower long edges of the resilient member.

* * * * *